United States Patent
Naya et al.

(10) Patent No.: US 9,645,087 B2
(45) Date of Patent: May 9, 2017

(54) MEASURING APPARATUS WHERE A DISTANCE BETWEEN A SURFACE OF A TRANSPARENT SUBSTRATE ON WHICH A MARKER PATTERN IS FORMED AND A FRONT SURFACE IS WITHIN A DEPTH OF FOCUS OF A DETECTING MEANS

(71) Applicant: FUJIFILM Corporation, Tokyo (JP)

(72) Inventors: Masayuki Naya, Ashigarakami-gun (JP); Shogo Yamazoe, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/668,584

(22) Filed: Mar. 25, 2015

(65) Prior Publication Data

US 2015/0198536 A1    Jul. 16, 2015

Related U.S. Application Data

(63) Continuation of application No. PCT/JP2013/005755, filed on Sep. 27, 2013.

(30) Foreign Application Priority Data

Sep. 28, 2012   (JP) ................... 2012-217669

(51) Int. Cl.
   *G01N 21/65*   (2006.01)
   *G01N 21/01*   (2006.01)
   *G01N 21/64*   (2006.01)

(52) U.S. Cl.
   CPC .......... *G01N 21/658* (2013.01); *G01N 21/01* (2013.01); *G01N 21/6402* (2013.01); *G01N 2201/02* (2013.01); *G01N 2201/06113* (2013.01)

(58) Field of Classification Search
   CPC .... G01N 21/648; G01N 21/658; G01N 21/01; G01N 2201/02; G01N 2201/06113; G01N 21/6402
   See application file for complete search history.

(56) References Cited

U.S. PATENT DOCUMENTS

| 2003/0231304 A1 | 12/2003 | Chan et al. |
| 2004/0161369 A1 | 8/2004 | Chan et al. |

(Continued)

FOREIGN PATENT DOCUMENTS

| JP | 2000-55809 A | 2/2000 |
| JP | 2002-168786 A | 6/2002 |

(Continued)

OTHER PUBLICATIONS

Ghadarghadr et al. "Plasmonic array nanoantennas on layered substrates: modeling and radiation characteristics", Optics Express, vol. 17, No. 21, pp. 18556-18570, Oct. 12, 2009.

(Continued)

*Primary Examiner* — Marcus Taningco
(74) *Attorney, Agent, or Firm* — Birch, Stewart, Kolasch & Birch, LLP (57) ABSTRACT

An optical electric field enhancing device is used with a measuring method which includes two-dimensionally scanning a surface in in-plane direction of the surface to detect, from the rear surface side of the device, signal light emitted from each scanning point when excitation light is applied, and obtaining a two-dimensional signal image on the surface based on the detected signal light. The device includes a transparent substrate, a marker pattern directly formed on the transparent substrate and extending in a direction non-parallel to the main scanning direction of the two-dimensional scanning, and fine uneven structures formed on the (Continued)

marker pattern and the transparent substrate where at least the surface is made of a metal film.

1 Claim, 3 Drawing Sheets

(56) References Cited

U.S. PATENT DOCUMENTS

| | | |
|---|---|---|
| 2005/0105085 A1 | 5/2005 | Naya |
| 2009/0079978 A1* | 3/2009 | Kimura .......................... 356/301 |
| 2012/0236301 A1 | 9/2012 | Hashimoto |
| 2013/0182248 A1 | 7/2013 | Naya et al. |
| 2013/0182343 A1 | 7/2013 | Naya et al. |

FOREIGN PATENT DOCUMENTS

| | | | |
|---|---|---|---|
| JP | 2003-248007 A | 9/2003 | |
| JP | 2005-172569 A | 6/2005 | |
| JP | 2006-514286 A | 4/2006 | |
| JP | 2006-145230 A | 6/2006 | |
| JP | 2007-147357 A | 6/2007 | |
| JP | 4347801 B2 | 10/2009 | |
| JP | 2012-63293 A | 3/2012 | |
| JP | 2012-63294 A | 3/2012 | |

OTHER PUBLICATIONS

International Search Report, issued in PCT/JP2013/005755, dated Feb. 4, 2014.
Written Opinion of the International Searching Authority, issued in PCT/JP2013/005755, dated Feb. 4, 2014.
Notification of Reasons for Refusal issued in Application No. JP 2012-217669, dated Oct. 27, 2015 with English Translation.

* cited by examiner

MEASURING APPARATUS WHERE A DISTANCE BETWEEN A SURFACE OF A TRANSPARENT SUBSTRATE ON WHICH A MARKER PATTERN IS FORMED AND A FRONT SURFACE IS WITHIN A DEPTH OF FOCUS OF A DETECTING MEANS

CROSS-REFERENCE TO RELATED APPLICATIONS

This application is a Continuation of PCT International Application No. PCT/JP2013/005755 filed on Sep. 27, 2013, which claims priority under 35 U.S.C. §119(a) to Japanese Patent Application No. 2012-217669 filed on Sep. 28, 2012. Each of the above applications is hereby expressly incorporated by reference, in its entirety, into the present application.

TECHNICAL FIELD

The present invention relates to an optical electric field enhancing device including a fine uneven structure made of a metal capable of inducing localized plasmons, a method of manufacturing the optical electric field enhancing device, and a measuring apparatus for detecting signal light enhanced with the optical electric field enhancing device and measuring physical properties of the signal light.

BACKGROUND ART

Optical electric field enhancing devices using the electric field enhancing effect of the localized plasmon resonance phenomenon on the surface of a metal have been known. With such an optical electric field enhancing device, when light is applied to a metal body, in particular, a metal body having nano-order protrusions and recesses on the surface, which is in contact with a sample, the optical electric fields on the surface are enhanced due to the localized plasmon resonance. When the optical electric field enhancing device is applied as a carrier (substrate) for carrying an analyte in a measuring apparatus which identifies and/or quantifies the analyte based on optical properties of signal light that is emitted from the analyte when light is applied, the signal light can be enhanced by the enhanced electric fields and highly sensitive measurement can be performed.

As a measuring method using the optical electric field enhancing device, surface enhanced Raman spectroscopy (SERS) is well known (see S. Ghadarghadr et al., "Plasmonic array nanoantennas on layered substrates: modeling and radiation characteristics", Optics Express, Vol. 17, No. 21, pp. 18556-18570, 2009, hereinafter Non-Patent Literature 1). The Raman spectroscopy is a method to obtain a spectrum (Raman spectrum) of Raman-scattered light by separating scattered light which is obtained by applying single wavelength light to a material, and is used to identify a material by detecting a Raman shift, to measure the concentration of an analyte in a sample based on Raman spectrum intensity, etc.

As the optical electric field enhancing device, a substrate which is formed by forming protrusions and recesses on the surface of a Si substrate and forming a metal film on the surface of the protrusions and recesses is mainly used (see PCT Japanese Publication No. 2006-514286, Japanese Patent No. 4347801, and Japanese Unexamined Patent Publication No. 2006-145230, hereinafter Patent Literature 1, 2, and 3, respectively).

Also, a substrate which is formed by anodizing a surface of an Al substrate to partially form a metal oxide layer ($Al_2O_3$), and filling a plurality of fine holes which are naturally formed in the surface of the metal oxide layer during the anodization with a metal has been proposed (see Japanese Unexamined Patent Publication No. 2005-172569, hereinafter Patent Literature 4).

Further, the present inventors have disclosed an optical electric field enhancing device wherein the surface of protrusions and recesses of a transparent fine uneven structure called boehmite is covered with a metal film, which optical electric field enhancing device allows detecting enhanced signal light at good S/N without the signal light being blocked by the sample when the sample is a μm-order or larger sample, such as cells (see Japanese Unexamined Patent Publication Nos. 2012-063293 and 2012-063294, hereinafter Patent Literature 5 and 6, respectively). According to this optical electric field enhancing device, the enhanced signal light can be detected from the rear surface side (the opposite surface from the surface carrying the sample) of the device, and this allows detecting the signal light enhanced by the enhanced optical electric fields without being blocked by the analyte.

On the other hand, a chemical imaging technique which performs multi-point measurement by scanning a sample on a carrier at regular point intervals (spatial resolution) and visualizes the results of the measurement to display a planar distribution image (map) is known. The chemical imaging allows intuitive understanding of distribution of components in the in-plane direction of the sample. Japanese Unexamined Patent Publication Nos. 2000-055809 and 2007-147357 (hereinafter, Patent Literature 7 and 8) have disclosed Raman spectrum imaging.

SUMMARY OF INVENTION

Technical Problem

The chemical imaging involves multi-point measurement by two-dimensional scanning. During two-dimensional scanning, there is a phenomenon where the start line in the sub-scanning direction does not become a straight line due to influence (jitter) of the clock, etc., of the apparatus, and it is necessary to perform jitter correction (removal) to obtain a highly accurate signal image. The jitter correction typically involves precision mechanical control, which requires an expensive control device, and therefore cost reduction is desired.

In view of the above-described circumstances, the present invention is directed to providing a measuring apparatus which allows chemical imaging that can obtain a highly accurate signal image without requiring precision mechanical control, and allows measurement at high S/N even when the sample is a μm-order or larger sample, such as cells, and an optical electric field enhancing device that allows providing such a measuring apparatus.

Solution to Problem

An optical electric field enhancing device of the invention is an optical electric field enhancing device for enhancing intensity of signal light which is emitted from a sample placed on the front surface of the device when excitation light is applied, wherein localized plasmons are induced on the front surface when the excitation light is applied, the optical electric field enhancing device being used with a measuring method which includes two-dimensionally scanning the front surface in in-plane directions of the surface with the excitation light, detecting, from the rear surface side of the device, the signal light from each scanning point, and obtaining a two-dimensional signal image on the front surface based on each signal light obtained by the detection, the optical electric field enhancing device comprising: a transparent substrate; a marker pattern directly formed on the transparent substrate and extending in a direction non-parallel to a main scanning direction of the two-dimensional scanning; and a fine uneven structure formed on the marker pattern and the transparent substrate wherein at least the front surface of the fine uneven structure is made of a metal film.

The term "transparent" as used herein refers to that the transmittance is 50% or more for the excitation light, and the light emitted from the analyte due to the excitation light. The transmittance for these light is preferably 75% or more, and more preferably 90% or more.

The transparent base substrate under the fine structure made of a metal covering at least the front surface has a transmittance of 50% or more to the excitation light applied to the base substrate and the light emitted from the analyte due to the excitation light. It is preferred that the transmittance for these light be 75% or more, and more preferably 90% or more.

The "sample placed" as used herein specifically refers to a sample that is in contact with or adjacent to the surface of the device, or a sample that is present in the vicinity of the surface of the device.

It is preferred that the fine uneven structure comprise a transparent fine uneven structure made of bayerite or boehmite and a metal film formed on the surface of protrusions and recesses of the transparent fine uneven structure.

A preferred aspect of the marker pattern is a linear pattern that is substantially perpendicular to the main scanning direction.

The marker pattern may be made of at least one material having a high reflectance to the excitation light selected from Cr, Au, Al, and Ag, may be made of at least one material having a high absorptance to the excitation light, such as carbon black or titanium nitride, or may be made of a material that emits fluorescence when the excitation light is applied.

A measuring apparatus of the invention comprises: the above-described optical electric field enhancing device of the invention; excitation light applying means for applying the excitation light to the front surface of the device where the sample is placed; scanning means for two-dimensionally scanning the front surface of the device in in-plane directions of the surface with the excitation light; detecting means for detecting, from the rear surface side of the device, the signal light from each scanning point; image obtaining means for obtaining the two-dimensional signal image and an image of the marker pattern on the front surface based on the signal light from each scanning point detected by the detecting means; image correcting means for correcting the obtained two-dimensional signal image based on the image of the marker pattern; and display means for displaying the two-dimensional signal image corrected by the image correcting means.

In the measuring apparatus of the invention, it is preferred that a distance between the surface of the transparent substrate on which the marker pattern is formed and the front surface of the fine uneven structure be within a depth of focus of the detecting means.

A method of manufacturing the optical electric field enhancing device of the invention comprises: preparing a transparent substrate; directly forming a marker pattern on the transparent substrate, the marker pattern extending in a direction non-parallel to a main scanning direction of the two-dimensional scanning; forming a metal film mainly composed of aluminum on the transparent substrate with the marker pattern formed thereon; forming a boehmite layer by immersing at least the metal film in water and then performing boiling treatment; and forming a metal film on the boehmite layer.

It is preferred that the marker pattern be formed by lithography.

Advantageous Effects of Invention

The optical electric field enhancing device of the invention includes a transparent substrate, a marker pattern directly formed on the transparent substrate and extending in a direction non-parallel to the main scanning direction of the two-dimensional scanning, and a fine uneven structure formed on the marker pattern and the transparent substrate wherein at least the front surface of the fine uneven structure is made of a metal film. When chemical imaging measurement is performed using the optical electric field enhancing device having the above-described structure, position shift in the two-dimensional image due to jitter of the applied excitation light can be corrected based on the amounts of position shifts in the image of the marker pattern, thereby obtaining a highly accurate signal image. Further, since the optical electric field enhancing device is made of a material that is transparent to the excitation light and the signal light, the signal light and the marker pattern can be detected from the rear surface side (the opposite side from the surface in contact with the sample) of the optical electric field enhancing device. Therefore, according to the invention, a highly accurate signal image can be obtained without requiring precision mechanical control, and chemical imaging can be performed at high S/N even when the sample is a μm-order or larger sample, such as cells.

DESCRIPTION OF EMBODIMENTS

Hereinafter, embodiments of a measuring method and a measuring apparatus of the present invention are described

Figure 1A:
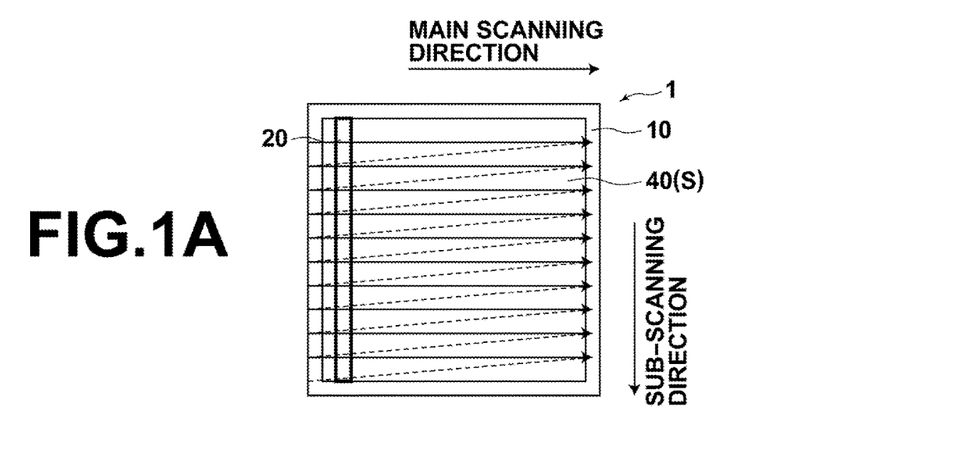
FIG. 1A is a schematic plan view illustrating one embodiment of an optical electric field enhancing device of the present invention.
Figure 1B:
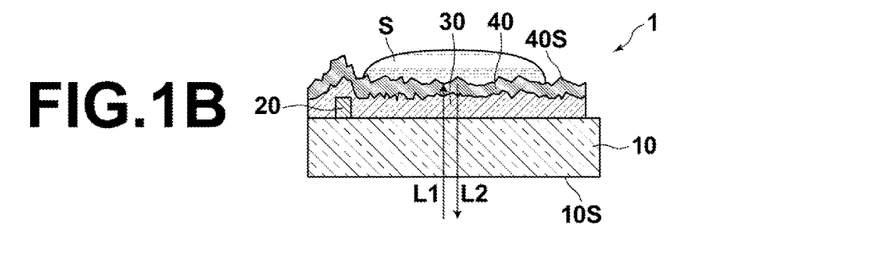
FIG. 1B is a schematic sectional view, taken along the thickness direction, illustrating one embodiment of the optical electric field enhancing device of the invention.

Optical Electric Field Enhancing Device and Measuring Apparatus Employing the Same FIG. 1A is a schematic plan view of an optical electric field enhancing device 1 according to one embodiment of the invention, and FIG. 1B is a schematic sectional view, taken along the thickness direction, of the optical electric field enhancing device 1.

As shown in FIG. 1A, the optical electric field enhancing device 1 is used for an imaging operation to perform two-dimensional scanning in the main scanning direction and the sub-scanning direction of a surface 40s on which a sample is placed and obtain a two-dimensional signal image on the surface based on signal light from each scanning point. As shown in FIG. 1B, localized plasmons are induced on the surface 40s when excitation light L1 is applied, and the intensity of signal light L2 emitted from the sample placed on the surface 40s when the excitation light L1 is applied is enhanced by the localized plasmons.

The optical electric field enhancing device 1 includes, on a transparent substrate 10, a marker pattern 20 directly formed on the transparent substrate 10, a transparent fine uneven structure 30 formed on the transparent substrate 10 and the marker pattern 20, and a fine uneven structure 40 made of a metal film formed on the transparent fine uneven structure 30. The signal light L2 from each scanning point is detected from the rear surface 10s side of the device 1.

The transparent substrate 10 is not particularly limited provided that it is transparent; however, the transparent substrate 10 with higher transparency is more preferred, and examples thereof include glass, acrylic resin, etc. The transparent substrate 10 may have a single layer structure or a multi-layer structure. An example of the multi-layer substrate is a glass substrate with a $TiO_2$ film formed thereon as a protective film.

The marker pattern 20 is not particularly limited provided that it emits the signal light L2 when the excitation light L1 is applied and allows obtaining a two-dimensional signal image with an image obtaining means, which will be described later. Examples of the material thereof include a material having a high reflectance to the excitation light L1, a material having a high absorptance to the excitation light L1, a material that emits fluorescence when the excitation light L1 is applied, etc.

Examples of the material having a high reflectance to the excitation light L1 are metals, such as Cr, Au, Ag, Al, etc. The marker pattern 20 is preferably made of at least one metal selected from Cr, Au, Al, and Ag, and particularly preferably Cr.

Examples of the material having a high absorptance to the excitation light L1 include carbon black, silicon nitride, etc.

Further, fluorescence is not likely to be cut by a wavelength selective filter which is disposed in the optical path to a detector, and can be used as a marker formed only on a specific area.

The marker pattern 20 is used to correct (remove) the phenomenon where the start line in the sub-scanning direction does not become a straight line due to influence (jitter) of the clock, etc., of the apparatus to obtain a highly accurate signal image, and the correction cannot be achieved by using a pattern extending in a direction parallel to the main scanning direction. In this view, the marker pattern 20 has a pattern extending in a direction non-parallel to the main scanning direction, and a preferred pattern is a line that is substantially perpendicular to the main scanning direction, as shown in FIG. 1A, in view of ease of correction.

Figure 2A:
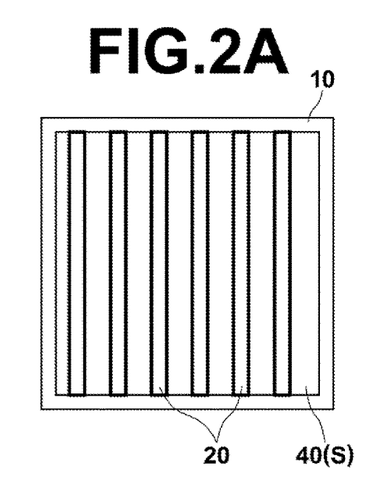
FIG. 2A is a schematic plan view illustrating another embodiment of the optical electric field enhancing device of the invention.
Figure 2B:
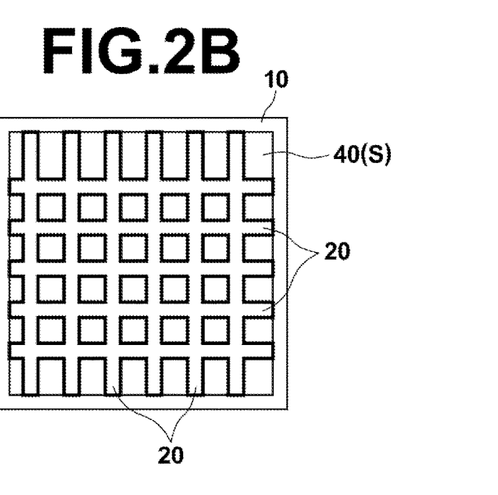
FIG. 2B is a schematic plan view illustrating yet another embodiment of the optical electric field enhancing device of the invention, FIG. 3 show sectional views, taken along the thickness direction, illustrating one embodiment of a method of manufacturing the optical electric field enhancing device of the invention.

Besides the pattern shown in FIG. 1A, a stripe pattern as shown in FIG. 2A or a lattice pattern as shown in FIG. 2B can be used. The stripe pattern allows finer correction, and the lattice pattern is also effective to correct jitter in the sub-scanning direction. A fine pattern such as a checkerboard pattern is effective to perform measurement to precisely identify a local position.

It is preferred that the marker pattern 20 have a thickness of 50 nm or more to allow highly sensitive detection of the signal light.

The transparent fine uneven structure 30 is not particularly limited provided that it has an average depth and an average pitch that allows inducing localized plasmons on the surface of the fine uneven structure 40 which is the surface of the metal film formed on the transparent fine uneven structure 30. The transparent fine uneven structure 30 is preferably a bayerite layer or a boehmite layer, and is most preferably a boehmite layer in view of ease of film formation and high in-plane uniformity of the uneven structure. In the aspect where the optical electric field enhancing device 1 uses boehmite, the surface uneven structure has high in-plane uniformity, and this allows obtaining highly reproducible data when measurements are conducted on the same sample with applying the light to different positions on the sample. This allows improving the reliability of data by obtaining pieces of data of the same sample with applying the light to different positions on the sample.

Another example of the transparent fine uneven structure 30 is an anodized aluminum film which is obtained by anodizing aluminum and then removing unanodized portions of the aluminum. Although the transparent substrate 10 and the transparent fine uneven structure 30 are made of different materials in the aspect shown in this embodiment, the transparent fine uneven structure 30 may be formed by processing the surface of the transparent substrate 10. In this case, the transparent fine uneven structure 30 is integrated with the transparent substrate 10. This arrangement can be achieved by conducting lithography and dry etching on the surface of a glass substrate, for example.

The fine uneven structure 40 made of a metal film is not particularly limited; however, the fine uneven structure 40 is preferably made of a metal which is capable of inducing good localized plasmons when the excitation light L1 is applied. Examples of such a metal include Au, Ag, Cu, Al, Pt, and alloys mainly composed of any of these metals, and Au is particularly preferred.

The average size and the average pitch of the protrusions of the protrusions and recesses of the fine uneven structure 40 made of a metal film are not particularly limited provided that the fine uneven structure 40 made of a metal film is capable of inducing localized plasmons on the surface when the excitation light L1 is applied. However, it is preferred that the average size and the average pitch be smaller than the wavelength of the excitation light L1. It is desirable that the fine uneven structure 40 made of a metal film has an average depth of 200 nm or less from the apexes of the protrusions to the bottoms of the recesses adjacent to the protrusions, and an average pitch of 200 nm or less between the apexes of the protrusions adjacent to each other with the recess therebetween.

The fine uneven structure 40 made of a metal film may have a fine uneven structure depending on the uneven structure 30 formed on the base substrate, as in this embodiment, or may have a fine uneven structure that does not depend on the surface shape of the base substrate where the base substrate used has high surface smoothness. However, since a metal easily form aggregates, etc., the shape of the fine uneven structure depending on the uneven structure formed on the base may not necessarily be the same as the shape of the base.

In view of the focal point on the marker pattern 20 and on the sample, one may think that it is preferred to form the marker pattern 20 on the fine uneven structure 40 made of a metal film. However, patterning of the marker on the very thin nano-order fine uneven structure tends to cause cracking in the fine uneven structure and is difficult in view of manufacturing. According to the arrangement of this embodiment, a marker pattern having an accurate shape can be formed without influencing the fine uneven structure.

It is preferred that the thicknesses of the layers of the marker pattern 20, the transparent fine uneven structure 30, and the fine uneven structure 40 made of a metal film of the optical electric field enhancing device 1 are designed such that highly sensitive detection of the signal light L2 (such as reflected light or absorbed light) from the marker pattern 20 and the sample S can be achieved from the rear surface 10s side of the device 1. It should be noted that it is not necessary to consider the thickness of the transparent substrate 10, which is large and is on a different order of magnitude (the substrate is on the order of a millimeter and the other layers are on the order of nanometers).

To enable highly sensitive detection from the rear surface 10s side of the signal light from the marker pattern 20 and the sample S, it is necessary that the front surface, on which the marker pattern 20 is directly formed, of the substrate 10 and the surface 40s of the fine uneven structure 40 made of a metal film are present within the depth of focus of the optical system for detecting the signal light.

It is therefore necessary to design the total film thickness of the transparent fine uneven structure 30 and the fine uneven structure 40 made of a metal film with taking the depth of focus of the optical system used for the detection into account.

For example, in a case where the device of the invention is applied to a Raman spectroscopic apparatus, a laser of 780 nm is used as the excitation light, and the depth of focus of the system which detects from the transparent substrate 10 side through a microscope lens having a magnitude of 100× and a numerical aperture of 0.9 is about 700 nm. In this case, the total film thickness of the transparent fine uneven structure 30 and the fine uneven structure 40 made of a metal film is determined such that a sufficient electric field enhancing effect is obtained with a film thickness of 700 nm or less.

It is preferred that the average film thickness of the fine uneven structure 40 made of a metal film is within the range from 10 to 100 nm, in which localized plasmons can be well induced when the excitation light L1 is applied.

The thickness of the transparent fine uneven structure 30 is not particularly limited provided that it is determined with taking the depth of focus and the thickness of the metal film which can well induce localized plasmons described above into account, and a film thickness that is easy to produce is preferred. For example, in a case where a metal film having a thickness of 50 nm is formed on the transparent fine uneven structure 30 having a thickness of 200 nm, the total film thickness is 250 nm, and the surface of the substrate on which the marker is formed and the measurement surface formed by the fine structure of the metal are sufficiently within the depth of focus, and highly sensitive detection of both the reflected light from the marker and the signal light can be achieved.

Figure 3:
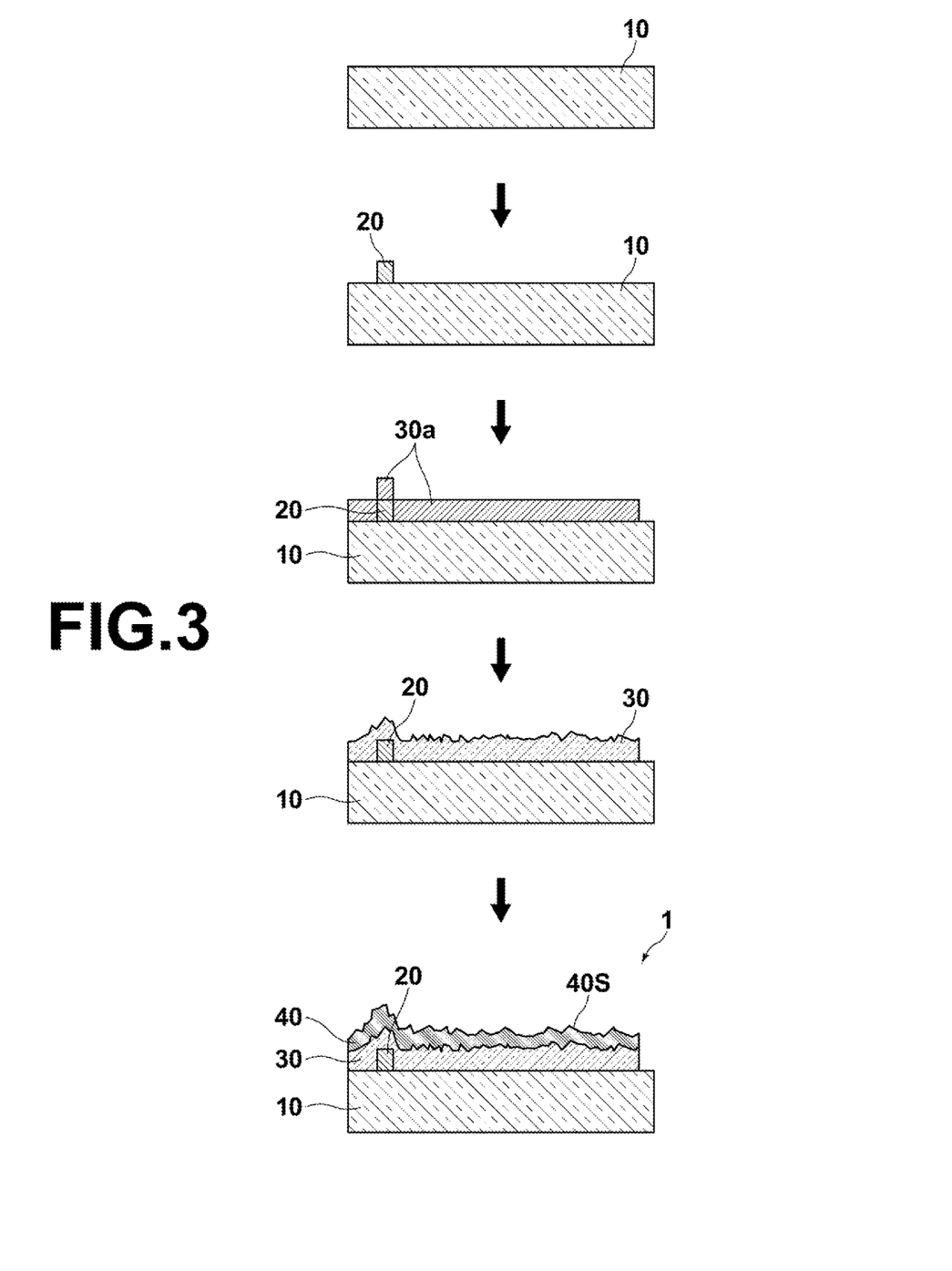

Next, as an example of a method for manufacturing the optical electric field enhancing device 1, an aspect where a boehmite layer is provided as the transparent fine uneven structure 30 is described with reference to FIG. 3.

First, the plate-like transparent substrate 10 is prepared, and the transparent substrate 10 is washed with pure water. Thereafter, the marker pattern 20 is formed.

The patterning method is not particularly limited; however, photolithography, which allows highly accurate patterning, is preferred.

Subsequently, the surface is washed with pure water. Then, an aluminum layer 30a having a thickness on the order of several tens nanometers is formed by sputtering on the surface of the transparent substrate 10 and the surface of the marker pattern 20.

Subsequently, the transparent substrate 10 provided with the aluminum layer 30a is immersed in boiled pure water, and is removed from the boiled pure water after several minutes (around five minutes). This boiling treatment (boehmite treatment) makes the aluminum layer transparent to thereby form the transparent fine uneven structure (boehmite layer) 30.

On the thus obtained boehmite layer 30, a metal film, such as Au is formed by vapor deposition, and thus the optical electric field enhancing device 1 including the fine uneven structure 40 made of a metal at least on the surface is obtained. It should be noted that the method used to form the metal film 40 is not limited to vapor deposition, and the metal film may be formed by immobilizing metal fine particles, for example. Further, the vapor deposition is not limited to a usual vapor deposition method, and an oblique vapor deposition method may be used.

The optical electric field enhancing device can be manufactured as described above.

Figure 4:
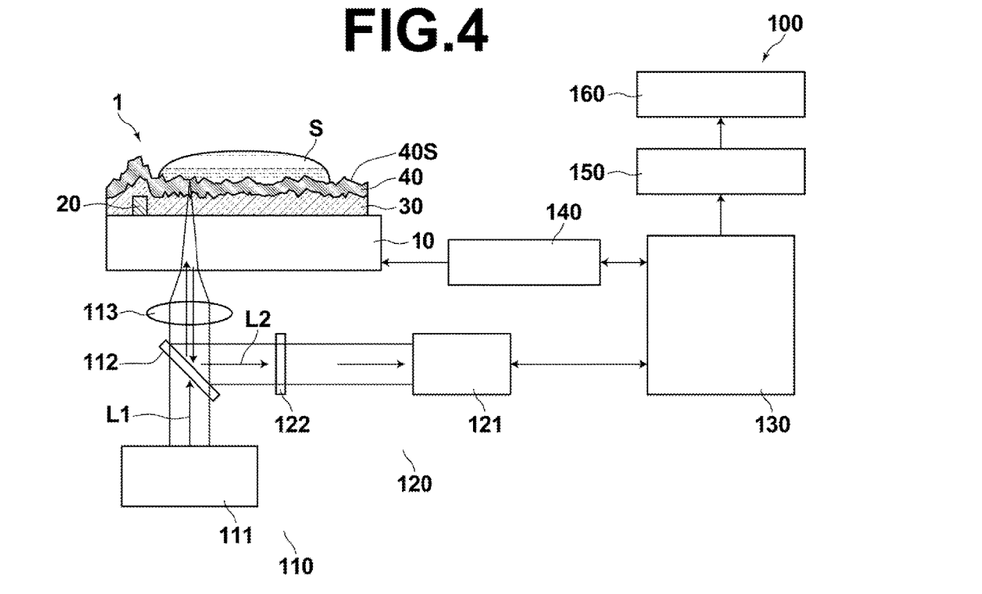
FIG. 4 is a schematic sectional view illustrating one embodiment of a measuring apparatus employing the optical electric field enhancing device of the invention.

Next, a measuring apparatus 100 that performs imaging using the optical electric field enhancing device 1 is described. FIG. 4 is a schematic sectional view illustrating the configuration of the measuring apparatus 100.

As shown in FIG. 4, the measuring apparatus 100 includes: the optical electric field enhancing device 1 with a sample S placed on the surface 40s thereof; an excitation light applying means 110 which applies the excitation light L1 to the sample S from the rear surface 10s side (the transparent substrate 10 side) of the optical electric field enhancing device 1; a scanning means 140 which performs two-dimensional scanning in the in-plane direction of the device 1 with the excitation light L1; a detecting means 120 which detects, from the rear surface 10s side, the signal light L2 from each scanning point, which signal light L2 is emitted from the analyte in the sample S and enhanced by operation of the optical electric field enhancing device 1; an image obtaining means 130 which obtains a two-dimensional signal image and a marker pattern image on the surface 40s based on the signal light L2 from each scanning point detected by the detecting means 120; an image correcting means 150 which corrects the obtained two-dimensional signal image based on the image of the marker pattern 20; and a display means 160 which displays the two-dimensional signal image corrected by the image correcting means 150.

As described previously, in the optical electric field enhancing device 1 used in the measuring apparatus of the invention, the distance between the surface of the transparent substrate 10 on which the marker pattern is formed and the surface 40s of the fine uneven structure is designed to be within the depth of focus of the detecting means.

The excitation light applying means 110 includes: an excitation light source 111 which emits the excitation light L1; a dichroic mirror 112 which transmits the excitation light L1 through to the substrate 10 and reflects light from the substrate 10, which contains the enhanced signal light L2 emitted from the analyte in the sample S when the excitation light L1 is applied, to the light detection unit 120; and a lens 113 which collects the excitation light L1 transmitted through the dichroic mirror 112 onto the area of the optical electric field enhancing device 1 on which the sample S is placed and collimates light from the sample.

The excitation light applying means 110 may include, as necessary, a laser line filter, or the like, which makes the light L1 emitted from the excitation light source 111 into excitation light of a specific wavelength.

The light detecting means 120 includes: a notch filter 122, which is disposed on the rear surface side of the transparent substrate 10, absorbs the excitation light L1 in the light containing the signal light L2 and transmitted through the dichroic mirror 112, and transmits the remaining light; and a photodetector 121, such as a spectroscope. It is preferred that the light detecting means 121 includes, between the notch filter 122 and the light detector 121, a slit and a pair of lenses which remove noise light and collimate and direct the signal light L2 to the photodetector 121, such as a spectroscope. In an aspect where a spectroscope is provided and Raman-scattered light is detected, incoming Raman-scattered light Ls is separated to obtain a Raman spectrum.

The detection by the photodetector 120 is performed at each of scanning points which are arranged at a predetermined interval and scanned with the excitation light in the main scanning direction and the sub-scanning direction shown in FIG. 1 by the scanning means 140. Then, the results of detection, such as intensity and spectrum, of the signal light L2 detected at each scanning point are sent to the image obtaining means 130.

The image obtaining means 130 obtains a two-dimensional signal image and a marker pattern image on the surface 40s based on the result of detection at each scanning point. For example, in a case where the obtained results of detection are spectroscopic results, such as Raman spectra, two-dimensional imaging can be achieved by determining a desired wavelength among the obtained spectrum pattern, and displaying the obtained signal at the position corresponding to each scanning point on the surface 40s to visualize the results of detection of Raman spectra.

However, the two-dimensional image obtained at this stage contains position shifts due to jitter. The measuring apparatus 100 obtains the two-dimensional image of the marker pattern 20 in addition to the two-dimensional image with respect to the sample. A schematic diagram of the image obtained by the image obtaining means 130 of the measuring apparatus 100 is shown on the lift in FIG. 5.

Figure 5:
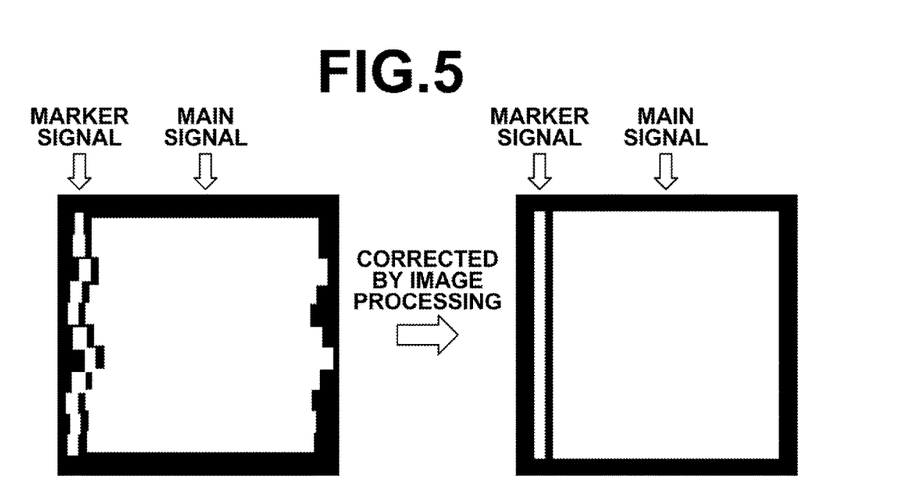
FIG. 5 is a schematic diagram illustrating a marker pattern image before processing by image correcting means of the measuring apparatus of the invention (left) and a marker pattern image after processing by the image correcting means (right).

As shown in the drawing, position shifts due to jitter contained in the image is the same as position shifts due to jitter contained in the image of the marker signal. The image correcting means 150 stores a correct marker signal image in advance, and corrects the two-dimensional signal image obtained by the image obtaining means 130 such that the measured marker signal image is corrected based on the correct marker signal image, thereby obtaining a corrected two-dimensional signal image from which the position shifts due to jitter are removed.

The two-dimensional signal image corrected by the image correcting means 150 is sent to the display means 160, which displays the two-dimensional signal image as a correct two-dimensional signal image, as shown on the right in FIG. 5.

The optical electric field enhancing device 1 and the measuring apparatus 100 employing the optical electric field enhancing device 1 are preferably usable for chemical imaging of Raman-scattered light, fluorescence, higher harmonic, Rayleigh scattered light, Mie scattered light, etc.

The optical electric field enhancing device 1 includes the transparent substrate 10, the marker pattern 20 directly formed on the transparent substrate 10 and extending in the main scanning direction and the non-parallel direction of the two-dimensional scanning, and the fine uneven structures (30, 40) formed on the marker pattern 20 and the transparent substrate 10 where at least the surface 40s is made of a metal film 40. When chemical imaging measurement is performed using the optical electric field enhancing device having the above-described structure, position shifts in the two-dimensional image due to jitter of the applied excitation light L1 can be corrected based on the amounts of position shifts in the image of the marker pattern 20, thereby obtaining a highly accurate signal image. Further, since the optical electric field enhancing device 1 is made of a material that is transparent to the excitation light L1 and the signal light L2, the signal light L2 from the sample and the marker pattern 20 can be detected from the rear surface 10s side (the opposite side from the surface in contact with the sample) of the optical electric field enhancing device. Therefore, according to the invention, a highly accurate signal image can be obtained without requiring precision mechanical control, and chemical imaging can be performed at high S/N even when the sample is a μm-order or larger sample, such as cells.

Modifications

In the above-described embodiments, the excitation light applying means 110 and the light detection means 120 are disposed on the rear surface side of the optical electric field enhancing device 1, and the excitation light is applied from the rear surface side. However, the excitation light applying means 110 may be disposed on the front surface side (the surface on which the analyte is placed) of the optical electric field enhancing device 1, and the excitation light may be applied from the front surface side. The localized plasmon resonance can be similarly induced and the optical electric field enhancing effect can be similarly obtained when the excitation light is applied from either of the front surface side or the rear surface side of the fine uneven structure made of a metal of the optical electric field enhancing device.

What is claimed is:

1. A measuring apparatus comprising:
an optical electric field enhancing device for enhancing intensity of signal light which is emitted from a sample placed on the front surface of the device when excitation light is applied, wherein localized plasmons are induced on the front surface when the excitation light is applied, the optical electric field enhancing device being used with a measuring method which includes two-dimensionally scanning the front surface in in-plane directions of the surface with the excitation light, detecting, from the rear surface side of the device, the signal light from each scanning point, and obtaining a two-dimensional signal image on the front surface based on each signal light obtained by the detection, the optical electric field enhancing device comprising: a transparent substrate; a marker pattern directly formed on the transparent substrate and extending in a direction non-parallel to a main scanning direction of the two-dimensional scanning; and a fine uneven structure formed on the marker pattern and the transparent substrate, wherein at least the front surface of the fine uneven structure is made of a metal film;

excitation light applying means for applying the excitation light to the front surface;

scanning means for two-dimensionally scanning the front surface in in-plane directions of the surface with the excitation light;

detecting means for detecting, from the rear surface side of the device, the signal light from each scanning point;

image obtaining means for obtaining the two-dimensional signal image and an image of the marker pattern on the front surface based on the signal light from each scanning point detected by the detecting means;

image correcting means for correcting the obtained two-dimensional signal image based on the image of the marker pattern; and display means for displaying the two-dimensional signal image corrected by the image correcting means;

wherein a distance between the surface of the transparent substrate on which the marker pattern is formed and the front surface is within a depth of focus of the detecting means; and wherein the rear surface of the photoelectric field enhancing device is outside the depth of focus and the marker pattern provided on a marker pattern formation surface of the transparent substrate and the surface of the fine uneven structure are within the depth of focus.

* * * * *